United States Patent [19]

Akhavi

[11] Patent Number: 4,551,864
[45] Date of Patent: Nov. 12, 1985

[54] ANTERIOR CHAMBER LENS

[75] Inventor: David S. Akhavi, Westwood, Calif.

[73] Assignee: Iolab Corporation, Covina, Calif.

[21] Appl. No.: 524,276

[22] Filed: Aug. 18, 1983

[51] Int. Cl.$^4$ ............................................. A61F 1/16
[52] U.S. Cl. ...................................................... 623/6
[58] Field of Search ............................................... 3/13

[56] References Cited

U.S. PATENT DOCUMENTS

| 1,953,604 | 4/1934 | Heller | 273/80.4 |
|---|---|---|---|
| 2,018,897 | 10/1935 | Reach | 273/80.4 |
| 4,249,271 | 2/1981 | Polev | 3/13 A |
| 4,338,687 | 7/1982 | Rainin | 3/13 A |
| 4,403,354 | 9/1983 | Rainin | 3/13 A |
| 4,503,570 | 3/1985 | Grendahl | 3/13 A |

Primary Examiner—Richard J. Apley
Assistant Examiner—James Prizant
Attorney, Agent, or Firm—Donal B. Tobin

[57] ABSTRACT

A universal anterior chamber lens having an optic with bores entering into the edge of the optic at points spaced circumferentially apart about 180°. The optic is supported in the anterior chamber by haptics, each of which have a first end fixed to the optic, a first leg extending from the optic to the peripheral anatomy of the eye, a second leg extending transverse to the optic in contact with the anatomy of the eye and a third leg extending back toward the optic. The first leg includes a concave spring-like section extending toward the third leg. The free end of the third leg extends into the bore provided in the optic so that as the haptics compress, the free end of the haptic can ride freely in the optic bore. A locking mechanism holds the free end of the haptic in the bore.

5 Claims, 5 Drawing Figures

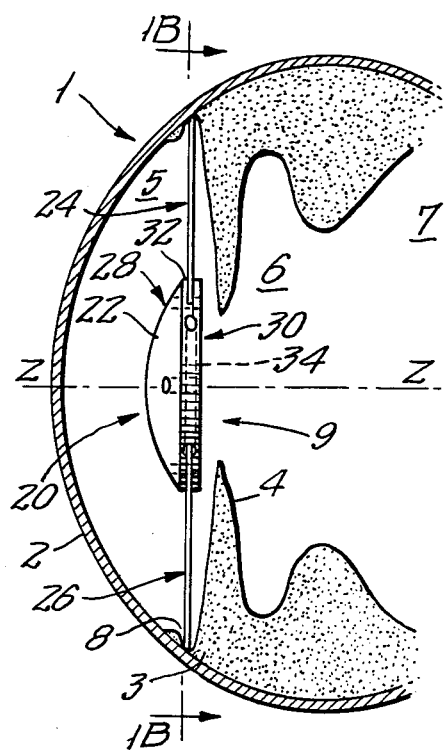
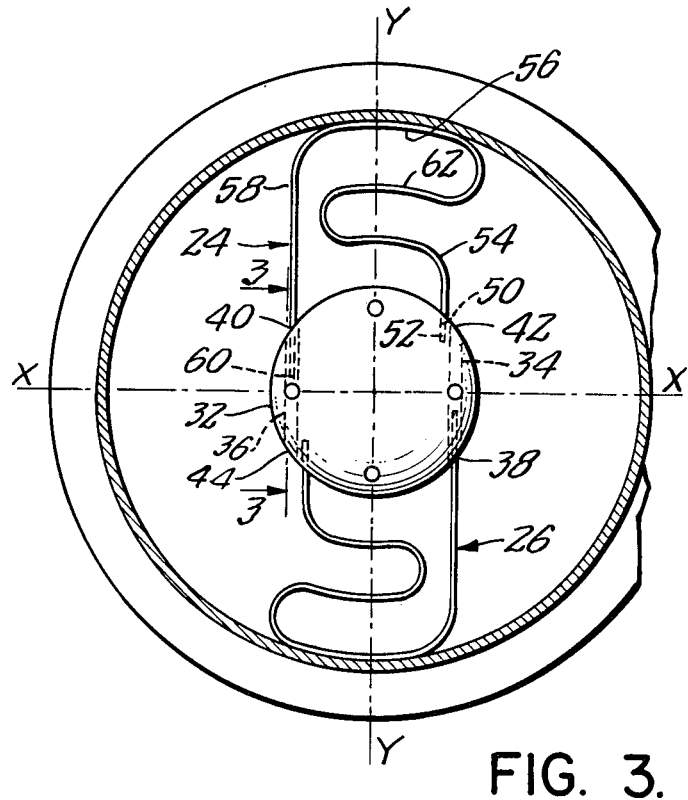
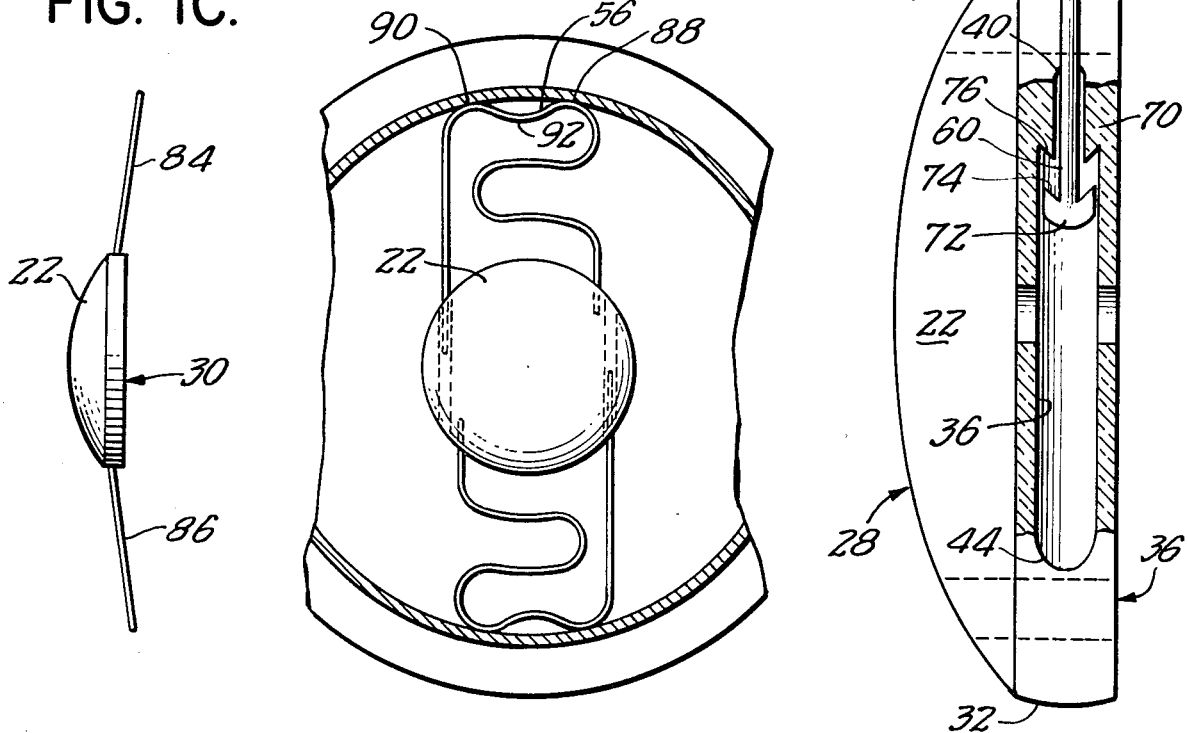

ANTERIOR CHAMBER LENS

FIELD OF THE INVENTION

The present invention relates to an anterior chamber intraocular lens and, more particularly, a universal anterior chamber lens which may fit many sized eyes within the range of the usual variation in eye sizes.

BACKGROUND OF THE INVENTION

It is now commonly accepted that the vision impairing disease known as cataracts can be alleviated by surgically replacing the natural lens of the eye with an artificial intraocular lens.

The anatomy of the eye 1 is shown schematically in FIG. 1A. The cornea 2 forms the front surface of the eye and connects with the ciliary muscle 3, from which the iris 4 extends. Iris 4 divides the front portion of the eye into the anterior chamber 5, between the iris 4 and cornea 2, and a posterior chamber 6 behind iris 4. A circumferential groove in the vicinity of ciliary muscle 3, anterior of iris 4 is the anterior chamber angle 8. Pupil 9 is the aperture at the center of iris 4 through which light passes to posterior chamber 6 and the back of the eye. The natural lens of the eye (not shown) is supported in posterior chamber 6 by suspensory ligaments (also not shown). The remainder of the eye 7 is called the vitreous chamber through which light passes to reach the retina, from which the image is sensed by the optic nerve.

A variety of lens assemblies are available for implantation in the eye. Specific lenses have been designed for placement in anterior chamber 5 of the eye. Other lenses have been specifically designed for placement in posterior chamber 6 and other lenses have been designed for attachment directly to the iris 4.

The dimensions of the human eye vary significantly from person to person. Thus, intraocular lens manufacturers must provide lenses in a variety of sizes to fit different people. It would be desirable to have a single, universal lens which would fit a variety of eye sizes.

Intraocular lenses have two principal parts: a medial, light-focusing body (also called the optic) made of a nontoxic, plastic material which will replace the natural lens of the eye and focus light on the retina, and haptic support portions which extend from the optic to the anatomy of the eye and provide a means for fixing and holding the optic in its proper position within the eye. The haptic portions must control the position of the optic along orthogonal axes X, Y and Z,; shown in FIGS. 1A and 1B. Proper centration with respect to the X and Y axes is important to keep the optic properly aligned with pupil 9. If the center of the optic gets too far away from the intersection of the X and Y axes, the optic is said to be decentered, so only a portion of the light impinging on the optic will be properly focused through the pupil onto the retina.

It is also important to control the motion of the optic along the Z axis. Particularly with an anterior chamber lens, it is important to prevent the optic from touching the anterior surface of iris 4, and it is important to prevent the optic from touching the posterior surface of cornea 2. Thus, the haptics must support the optic a preferred distance away from iris 4 and cornea 2. It is also important to prevent the lens from tilting, that is rotating to any substantial degree, about either the X or Y axes. Such tilting prevents the light from being properly focused by the optic on the retina.

Especially for an anterior chamber lens, it is also important that the lens can accommodate the natural deformation which the eye experiences in routine daily activity caused, for example, by rubbing the eye, running or falling.

A relatively early version of an anterior chamber lens is shown in U.S. Pat. No. 2,834,023, which includes an optic and a wire or plastic haptic glued into an open groove on the edge of the optic. The ends of the haptic are mounted in the angle of the eye. The haptic is a rod-like configuration formed into flexible loops or wings to support the optic against undesirable movement in the anterior chamber while at the same time permitting flexing to accommodate the stresses induced by normal movement of the eye. In more recent designs, as shown, for example, in U.S. Pat. Nos. 4,087,866 and 4,261,065, anterior chamber lenses have been made as a single piece, with the optic and the supporting haptic structure formed of the same material. These solid unitary haptics provide very good control for the optic against decentering tilting or vaulting. However, they are less flexible and, thus, must be very carefully fitted to the eye.

One attempt to properly fit an anterior chamber intraocular lens is shown in U.S. Pat. No. 4,134,160 where one of the haptic feet is formed in two pieces with an adjustable tab which can be slid out to the proper radius to fit the eye and then crimped into position.

U.S. Pat. No. 4,370,760 is an attempt to make a universal anterior chamber lens which has a greater degree of flexibility than the previously described anterior chamber lenses but which is stated to achieve control over motion of the optic along the Z axis between the iris and the cornea. This is also a one-piece lens where the optic and the haptic portions are made of the same unitary material.

One-piece lenses can be difficult and expensive to manufacture. The lens shown in U.S. Pat. No. 4,159,546, popularly known as the Shearing or J-loop lens, has what is called open-loop haptic supports made of flexible, memory retaining, polypropylene filament, which act like springs. This lens is easy and relatively inexpensive to manufacture. This lens has had great popular acceptance and achieves excellent results. However, it is used principally in the posterior chamber of the eye.

It would be very desirable to have a single universal anterior chamber lens to fit a variety of eye sizes which had the great flexibility of open-loop lenses but which, at the same time, provided a high degree of control over the motion of the optic provided by the one-piece anterior chamber lenses.

SUMMARY OF THE INVENTION

The present invention is a universal, anterior-chamber lens which provides very good flexibility of the haptic supports and at the same time provides good control over the motion of the optic in the anterior chamber to control centration, tilt and vault. The anterior chamber intraocular lens of the present invention includes an optic having an anterior and a posterior surface and a surrounding circumferential edge. The optic has at least one bore entering the optic at the edge and extending into the optic. In an alternative construction, the bore can extend straight through the optic and exit at another portion of the edge of the optic. The lens of the present invention has at least one flexible, resilient filamentary haptic which extends from the optic for engaging the peripheral anatomy of the eye and which has a first end fixed to the optic at a point spaced circumferentially from the above-mentioned bore and has a second end extending into the bore and freely slidable in the bore.

In the preferred embodiment of the lens of the present invention, there are two such flexible haptics and two bores. When these flexible loops are in their relaxed state, their outside dimension is slightly greater than the diameter of the largest eye into which it would be placed. When the lens is compressed either to fit a small eye or to accommodate the natural motion of the eye, the second end of the haptic will slide freely within the optic bore to permit the dimensions of the lens to change very easily without subjecting the surrounding anatomy of the eye to any undue forces. However, the multiple point contact of the haptics with the optic provide good control over the optic in the anterior chamber.

A variety of configurations can be used for the haptic loops. In the preferred embodiment, the haptics have a first leg extending from the first end of the haptic which is fixed to the optic, and a second leg extending transverse to the optic for engaging the peripheral anatomy of the eye and a third leg extending from the second leg to the free end of the haptic which is placed in the optic bore. The first, second and third legs are formed as a unitary haptic and have smooth connecting surfaces. The second leg can include two spaced-apart contact feet with a concave portion extending toward the optic connecting the contact feet. The first leg includes a concave portion extending back toward the third leg to provide a spring-like flexibility to the haptic and to facilitate the sliding motion of the free end of the thid leg in the bore of the optic with a minimum of binding. This concave portion also helps keep the second leg in contact with the peripheral anatomy of the eye when the haptic compresses.

In the preferred embodiment of the present invention a locking device is used to hold the free end of the haptics into the bore in the optic. This locking mechanism includes a flange formed by the portion of the optic surrounding the entry area to the bore for reducing the size of the bore in the entry area. The free end of the haptic includes an enlarged head larger than the bore in the entry area but smaller than the size of the remainder of the bore, so that the head may be forced past the flange into the remainder of the bore to restrain the second end from coming out of the bore. The enlarged head is preferably compressible so that as it is forced through the entry area flange, it will compress, and then as it clears the entry area flange, it will expand to restrain the enlarged head from being pulled through the entry area flange. The intraocular lens of the present design provides the great flexibility that can be provided by open-loop lenses but confines the free end of the open loop within the optic so that it will not touch the interior anatomy of the eye in any undesirable fashion. The haptic design facilitates flexibility but also provides good control over the optic to control centration, tilt and vault.

These and other features and advantages of the present invention will become more apparent when taken in conjunction with the following detailed description of the preferred embodiments and the following drawings.

BRIEF DESCRIPTION OF THE DRAWINGS

FIG. 1A shows a cross-sectional view of the anatomy of the eye with the lens of the present invention placed in the anterior chamber; and, FIG. 1B shows a front view of the anatomy of the eye and the lens of the present invention taken along lines 1B—1B in FIG. 1A;

FIG. 1C shows an alternative embodiment of the lens of the present invention;

FIG. 2 shows a further alternative embodiment of the lens of the present invention;

FIG. 3 shows a cross-sectional view of the optic portion of the lens taken along lines 3—3 in FIG. 1B.

DETAILED DESCRIPTION OF THE PREFERRED EMBODIMENT

Referring now to FIG. 1A, there is shown a cross-sectional view of the eye 1 with the intraocular lens of the present invention 20 placed in anterior chamber 5. The optic 22 is supported in front of pupil 9, and haptic loops 24 and 26 extend from the edge of optic 22 into anterior chamber angle 8. Haptics 24 and 26 hold optic 22 so that it is substantially centered on the X and Y axes of the eye.

Referring now to FIG. 1B, there is shown a front view of the eye taken along lines 1B—1B in FIG. 1A. Optic 22 is shown centered on the X and Y axes of the eye. The haptics 24 and 26 are shown extending to anterior chamber angle 8. Optic 22 has a convex anterior surface 28, a planar posterior surface 30 and a circumferential edge 32. Different shaped surfaces could be used for the anterior and posterior surfaces of optic 22.

Optic 22 has bores 34 and 36 entering edge 32 at points 38 and 40, respectively, placed circumferentially apart about 180° at substantially diametrically opposed positions. Bores 34 and 36 extend parallel to each other and parallel to the plane which is perpendicular to the optical axis of optic 22 (the Z axis). In this preferred embodiment, bores 34 and 36 extend in a straight line from entry portions 38 and 40, respectively, to exit optic 22 at exit areas 42 and 44, respectively, on edge 32 of optic 22. It is not necessary that bores 34 and 36 extend completely through optic 22, but as explained later, it is only necessary that bores 34 and 36 extend into optic 22 a sufficient distance to allow haptics 24 and 26 to compress and amount sufficient to permit lens 20 to fit a small eye and to accommodate the ordinary deformation of a small eye.

Haptics 24 and 26 are formed of a filamentary, resilient, memory-retaining plastic fiber, for example polypropylene or some other suitable plastic fibrous material which is resilient and has good spring-like qualities so that it may be easily deformed and return to its original shape when the deforming forces are reduced.

Still referring to FIG. 1B, haptic loop 24 has a first end 50 rigidly affixed to optic 22, usually by bonding end 50 within a bore 52 drilled into edge 32 of optic 22. Extending from first end 50 of haptic 24 is a first leg 54 which extends toward the peripheral anatomy of the eye. A second leg 56 extends from first leg 54 in a direction transverse to optic 22 for engaging the peripheral anatomy of the eye. It is preferable that second leg 56 extends a distance along the peripheral anatomy of the eye, that is anterior chamber angle 8 of the eye, a distance approximately equal to the diameter of optic 22. Haptic 24 includes a third leg 58 extending from the other end of second leg 56 back to optic 22. Free end 60 of leg 58 extends into bore 36 and slides freely within bore 36 so that as haptic 24 is compressed toward optic 22, free end 60 of haptic 24 slides freely within bore 36.

To provide additional flexibility to haptic 24, first leg 54 may include a concave section 62 extending in a direction transverse to optic 22 toward third leg 58. As haptic 24 compresses under the normal distortion of the eye, free end 60 will move into bore 36. Concave section 62 will also compress so as to keep second leg 56 in full contact with the peripheral anatomy of the eye in anterior chamber angle 8. Without concave section 62, when heptic 24 compressed, a portion of second leg 56 could have a tendency to move away from anterior chamber angle 8 and, thus, reduce the contact of haptic 24 with the peripheral anatomy of the eye, thus, reducing the control which haptic 24 would have over optic 22.

Haptic 26 is configured in the same shape as haptic 24, so that haptics 24 and 26 will be symmetrically disposed about optic 22.

Referring now to FIG. 3, there is shown a locking mechanism for securing free end 60 within bore 36. Entry portion 40 of bore 36 includes in inwardly extending flange 70 which reduces the size of bore 36 in entry area 40. The diameter of the hole in flange 70 is still large enough to permit third leg 58 of haptic 24 to slide freely through flange 70. Free end 60 of haptic 24 includes an enlarged head 72 which has a diameter greater than the diameter of flange 70 but less than the diameter of bore 36. The portion of enlarged head 72 which faces toward the third leg 58 may be undercut at point 74. The surface of flange 70 facing into bore 36 may include a cone-like projection 76 which corresponds generally to undercut 74 to form a barb for resisting the removal of free end 60 and head 72 from bore 36 through flange 70. Haptic 24, and particularly enlarged head 72, is made of a compressible plastic material so that head 72 may be inserted through flange 70 by forcing free end 60 into flange 70 and compressing enlarged head 72. When enlarged head 72 passes through the opening in flange 70, enlarged head 72 will expand so that undercut portions 74 will widen out wider than the diameter of the hole in flange 70, so that it will be difficult to remove the free ends 60 and enlarged head 72 back through the opening in flange 70. The diameter of enlarged head 72 is small enough so that it will slide freely within bore 36.

Referring now to FIG. 1C, there is shown an alternative embodiment of the intraocular lens of the present invention wherein haptics 84 and 86 extend posteriorly at a small angle to the posterior surface 30 of optic 22 in order to place optic 22 farther away from the anterior surface of iris 4 and somewhat closer to the posterior surface of cornea 2. The lens shown in FIG. 1C is a vaulted lens which will further reduce the possibility of chaffing between the posterior surface 30 of optic 22 and the anterior surface of iris 4.

Referring to FIG. 2 there is shown a further alternative embodiment of the lens of the present invention wherein the second leg 56 of haptic 24 has two contact portions 88 and 90 spaced apart by a concave portiion 92 which extends back toward optic 22. This configuration permits haptic 24 to contact anterior chamber angle 8 with a two-point contact at contact points 88 and 90 and to eliminate contact with angle 8 in the concave connecting portion area 92.

It will be appreciated that the present invention provides a universal anterior chamber intraocular lens which has a great deal of flexibility so that one lens can accommodate a large number of eye sizes. The use of filamentary haptics facilitates flexibility and the multiple point conact of the haptics with the optic provide good optic control against vaulting, decentering or tilting. Flexibility is further facilitated by permitting one end of the haptic to slide freely within a bore in the optic. Flexibility is further facilitated by including a concave portion in the haptic which holds the haptic in contact with the angle of the eye even as the haptic is compressed.

The present invention has been described in conjunction with preferred embodiments. Those skilled in the art will appreciated that many modifications and changes may be made to the preferred embodiments without departing from the present invention. It is, therefore, not intended to limit the present invention except as set forth in the appended claims.

I claim:

1. An anterior chamber intraocular lens comprising:
   an optic having an anterior surface, a posterior surface and a surrounding circumferential edge and having first and second bores entering at said edge of said optic at opposite peripheral portions of said edge, said bores extending substantially parallel to each other and extending into said optic generally parallel to the plane which is perpendicular to the optical axis of the optic;
   first and second flexible, resilient filamentary haptic means extending from said optic for engaging the peripheral anatomy of the eye;
   said first and second haptic means each having a first end and a second end;
   said first end of said first haptic means fixed to said optic at a point spaced circumferentially from said first bore an arc distance therealong of less than 180 degrees;
   said second end of said first haptic means extending into said first bore;
   said first end of said second haptic means fixed to said optic at a point spaced circumferentially from said second bore an arc distance therealong of less than 180 degrees, said second end of said second haptic means extending into said second bore;
   each of said first and second haptic means including
   (a) a first leg extending from said first end outwardly of said optic;
   (b) a second leg extending transversely of said optic for engaging the peripheral anatomy of the eye;
   (c) a third leg extending from said second leg to said second end of said haptic means;
   said first, second and third legs of each haptic forming a unitary haptic means and having smooth, connecting portions;
   each of said first legs of said first and second haptic means including a concave portion extending back toward said respective third leg to provide a greater flexibility to each of said first and second haptic means;
   each of said concave portions extending a distance toward said respective third leg so that a plane including the optical axis of said optic and intersecting said concave portion of said first haptic means will also intersect the concave portion of said second haptic means;

further including locking means cooperatively associated with each of said second ends of said first and second haptic means and the respective one of said first and second bores in said optic;

wherein a portion of said optic surrounding the entry area of each of said first and second bores extends thereinto to define a flange for reducing the size thereof in said entry area;

said second end of said first and second filamentary haptic means including an enlarged head larger than the respective first or second bores in said entry area but smaller than the remainder of the respective first or second bores so that said enlarged head may be forced past said flange into the remainder of said respective first or second bores to restrain the removal of said enlarged head of said second end from said respective first or second bores; and wherein said enlarged head and said flange are sufficiently resilient to permit said enlarged head to contract as it is forced through said flange and then to expand once it passes said flange and enters the remainder of said respective first and second bores.

2. The intraocular lens of claim 1 further including a cone projecting from said flange into the remainder of said respective first or second bores; and, a recess about said second end proximally of said enlarged head to provide a barb for restraining the withdrawal of said second end once said enlarged head is inserted through said flange.

3. The intraocular lens of claim 1 wherein said first end of said first haptic means is fixed to said optic at a point inward of and adjacent to the axis of the bore into which said second end of said second haptic means extends.

4. The intraocular lens of claim 1 wherein a portion of said first and second haptic for engaging the anatomy of the eye includes a pair of spaced contact feet and a concave portion extending toward said optic connecting said spaced contact feet.

5. An anterior chamber intraocular lens comprising:

an optic having an anterior surface, a posterior surface and a surrounding circumferential edge and having first and second bores entering at said edge of said optic at opposite peripheral portions of said edge, said bores extending substantially parallel to each other and extending into said optic generally parallel to the plane which is perpendicular to the optical axis of the optic;

first and second flexible, resilient filamentary haptic means extending from said optic for engaging the peripheral anatomy of the eye;

said first and second haptic means each having a first end and a second end;

said first end of said first haptic means fixed to said optic at a point spaced circumferentially from said first bore an arc distance therealong of less than 180 degrees;

said second end of said first haptic means extending into said first bore;

said first end of said second haptic means fixed to said optic at a point spaced circumferentially from said second bore an arc distance therealong of less than 180 degrees, said second end of said second haptic means extending into said second bore;

further including locking means cooperatively associated with each of said second ends of said first and second haptic means and the respective one of said first and second bores in said optic for permitting entry of said second end into the respective one of said first and second bores but restraining removal of said second end from the respective one of said first and second bores but permitting said second end to move freely within said respective one of said first and second bores;

a portion of said optic surrounding the entry area of each of said first and second bores extends thereinto to define a flange for reducing the size thereof in said entry area;

said second end of said first and second filamentary haptic means including an enlarged head larger than the respective first or second bores in said entry area but smaller than the remainder of the respective first or second bores so that said enlarged head may be forced past said flange into the remainder of said respective first or second bores to restrain the removal of said enlarged head of said second end from said respective first or second bores; and wherein said enlarged head and said flange are sufficiently resilient to permit said enlarged head to contract as it is forced through said flange and then to expand once it passes said flange and enters the remainder of said respective first and second bores.

* * * * *